(12) United States Patent
Aslam

(10) Patent No.: US 10,260,985 B2
(45) Date of Patent: Apr. 16, 2019

(54) METHODS FOR DETECTING LEAKS IN LIQUID PIPELINES

(71) Applicant: Naveed Aslam, Houston, TX (US)

(72) Inventor: Naveed Aslam, Houston, TX (US)

(73) Assignee: Linde Aktiengesellschaft, Munich (DE)

(*) Notice: Subject to any disclaimer, the term of this patent is extended or adjusted under 35 U.S.C. 154(b) by 98 days.

(21) Appl. No.: 15/596,497

(22) Filed: May 16, 2017

(65) Prior Publication Data

US 2018/0335363 A1  Nov. 22, 2018

(51) Int. Cl.
| | | |
|---|---|---|
| E21B 47/10 | (2012.01) | |
| E21B 47/11 | (2012.01) | |
| E21B 47/113 | (2012.01) | |
| G01M 3/18 | (2006.01) | |
| G01M 3/22 | (2006.01) | |
| G01N 21/75 | (2006.01) | |
| G01N 21/85 | (2006.01) | |
| G01N 15/06 | (2006.01) | |
| G01N 15/00 | (2006.01) | |

(52) U.S. Cl.
CPC ......... *G01M 3/222* (2013.01); *E21B 47/1025* (2013.01); *G01N 15/06* (2013.01); *G01N 21/85* (2013.01); *G01N 2015/0038* (2013.01); *G01N 2015/0046* (2013.01); *G01N 2015/0681* (2013.01); *G01N 2015/0693* (2013.01)

(58) Field of Classification Search
CPC ...... E21B 47/10; E21B 47/1025; E21B 47/11; E21B 47/113; G01M 3/18; G01M 3/22; G01M 3/222; G01N 21/75; G01N 21/85; G01N 2015/0038

See application file for complete search history.

(56) References Cited

U.S. PATENT DOCUMENTS

| | | | | |
|---|---|---|---|---|
| 5,983,736 A | * | 11/1999 | Gershman | G01M 3/22 73/865.8 |
| 2010/0060887 A1 | * | 3/2010 | Cho | B01D 65/104 356/237.3 |
| 2018/0172545 A1 | * | 6/2018 | Aslam | B08B 9/0555 |
| 2018/0292322 A1 | * | 10/2018 | Lecolier | G01N 21/6428 |

* cited by examiner

*Primary Examiner* — Nguyen Q. Ha
(74) *Attorney, Agent, or Firm* — Philip H. Von Neida

(57) ABSTRACT

A method for monitoring and detecting leaks in a pipeline is disclosed. The method is particularly useful in pipelines that are transporting hydrocarbons. Gas enabled photo sensitive particles are fed into the pipeline and when they encounter a leak, change their condition. This change is captured by a detector which transmits the data to an operator that a leak condition exists as well as its location and intensity.

28 Claims, 6 Drawing Sheets

INERT GAS STABILIZED ON MICRO SOLID PARTICLE

METHODS FOR DETECTING LEAKS IN LIQUID PIPELINES

BACKGROUND OF THE INVENTION

Hydrocarbons such as crude and other oils are frequently transported by pipelines. These pipelines are thousands of miles in total length and as a delivery infrastructure are aging in the United States. With this aging comes the need to inspect a pipeline to determine its integrity and maintain the pipeline assets with lowest possible cost.

Amongst the methods for inspecting pipelines are those used for detecting leaks in the pipeline. These range from manual inspection using trained dogs to advanced satellite based hyper spectral imaging. The various methods can be classified into non-optical and optical methods, or external (direct) and internal (inferential). The primary non-optical methods include acoustic monitoring, gas sampling, soil monitoring, flow monitoring and software based dynamic modeling.

Optical methods for leak detection can be classified as either passive or active. Active methods illuminate the area above the pipeline with a laser or a broadband source. The absorption or scattering caused by natural gas molecules above the surface is monitored using an array of sensors at specific wavelengths. If there is a significant absorption or scattering above a pipeline, then a leak is presumed to exist. The basic techniques for active monitoring include Tunable Diode Laser Absorption Spectroscopy (TDLAS), Laser Induced Fluorescence (LIF), Coherent Anti-Raman Spectroscopy (CARS), Fourier Transform Infrared Spectroscopy (FTIR) and evanescent sensing.

Passive monitoring of hydrocarbon leaks is similar to active monitoring in many aspects. However, the major difference between active and passive techniques is that passive techniques do not require a source. This makes passive systems less expensive. However, since a strong radiation source is not employed, many more expansive detectors and imagers have to be used with the passive systems. Two major types of passive systems used for monitoring leaks from hydrocarbon pipelines are thermal imaging and multi-wavelength imaging.

The method of leak detection selected for a pipeline is dependent on a variety of factors including pipeline characteristics, product characteristics, instrumentation and communications capabilities and economics.

Pipeline systems vary widely in their physical characteristics and operation functions and no one external or internal method is universally applicable or possesses all the features and functionality required for perfect leak detection performance.

The present invention provides for improved leak detection methods in hydrocarbon pipelines.

SUMMARY OF THE INVENTION

In one embodiment of the invention, there is disclosed a method for detecting a leak in a pipeline comprising feeding gas enabled photo sensitive particles into the pipeline.

In another embodiment of the invention, there is disclosed a method for monitoring a pipeline comprising feeding gas enabled photo sensitive particles into the pipeline.

The pipelines typically treated by the methods of the invention are those that are transporting hydrocarbons such as crude oils and other petrochemical products. The hydrocarbons are selected from the group consisting of crude oil, natural gas liquids, petrochemical products, monomers, particularly ethylene, and finished fuel products selected from the group consisting of diesel, gasoline and jet fuel.

The gas enabled photo sensitive particles are designed as particles which surround an inert gas such as nitrogen gas. The particles in turn are surrounded by a surfactant or liquid active system. This acts to provide a good formation of size and morphology of particles.

In one embodiment the gas enabled photo sensitive particles is an oil-gas-oil emulsion. The inert gas which is selected from the group of nitrogen and argon are entrapped in an outer hydrocarbon layer so that when photo sensitive particles are introduced into the crude pipeline system, they will get well mixed inside the crude bulk due to the outer hydrocarbon layer surrounding the inert gas core. The core is the inert gas and at the interface of the inert gas and hydrocarbon layer there can be preferably included a surfactant such as a non-ionic surfactant which will aid in stabilizing the hydrocarbon-inert gas interface.

The oil-gas-oil emulsion can thus be formed by assistance with certain surfactants such as sodium dodecyl sulfates, triblock copolymers PEO-PPO-PEO (poly(ethylene oxide)-poly(propylene oxide)-poly(ethylene oxide)), polyoxyethylene, alkylphenate, polytetrafluoroethylene (PTFE) and OTFE, ethoxylated alcohol, and polyethylene (PEG) surfactants.

A typical formulation could be a solid nano or micro silica or zinc oxide core particle on which a nitrogen or argon bubble could be stabilized thereby encapsulating the solid particle.

These photo sensitive particles can therefore be introduced into a pipeline through a small pulsating dosing pump at a point or intervals along the length of a pipeline.

When the gas enabled photo sensitive particles encounter a leak, they become quenched. This quenching takes place due to exposure of the particles to oxygen at the leak site thereby leading to the change of their luminescent characteristics and decline in their optical strength. This decline could be measured by counting the number of particles and loss of their specific signal strength due to the leak. This measurement could then be translated into calculating both the size of and location of the leak.

Detectors in/on the pipeline will send out a signal that is optical and as the density, light absorption and reflectivity of inert gas particles is different from the crude oil or other hydrocarbons, this bounce back is noted. An assessment of the state of affairs in the pipeline is then made and this information is transmitted to the supervisory control and data acquisition (SCADA) architecture through the detector measuring system. By virtue of establishing this steady state condition, readings that differ from this steady state will be evaluated by the SCADA to determine if a leak condition is present in the pipeline.

The detectors and their input into a SCADA architecture is a desirable feature for pipeline operators as these systems are in place. The data transmitting potential leak conditions can therefore be integrated into the SCADA and provide information to the operator in a control room based on these systems already in place.

The detectors can be mounted through a flange or instrument port in the pipeline. A typical pipeline has pressure, flow and temperature measurement ports so the detectors for the particles could be inserted into these ports and measurements made. This relieves the operator of adding additional ports or other devices needed for incorporating the detectors into the pipeline.

In addition, a number of detectors could be employed such that as a leak happens, the number of active particles will decrease as some of the particles will be lost at the leak site. This number could be counted through a simple counter and could be correlated with leak site size and location due to measuring this difference in particle numbers.

The detectors can be mounted as far as 10 miles apart in a given pipeline with detection occurring continuously. Depending upon operations, active particles could be introduced once a week for example.

DETAILED DESCRIPTION OF THE INVENTION

Figure 1:
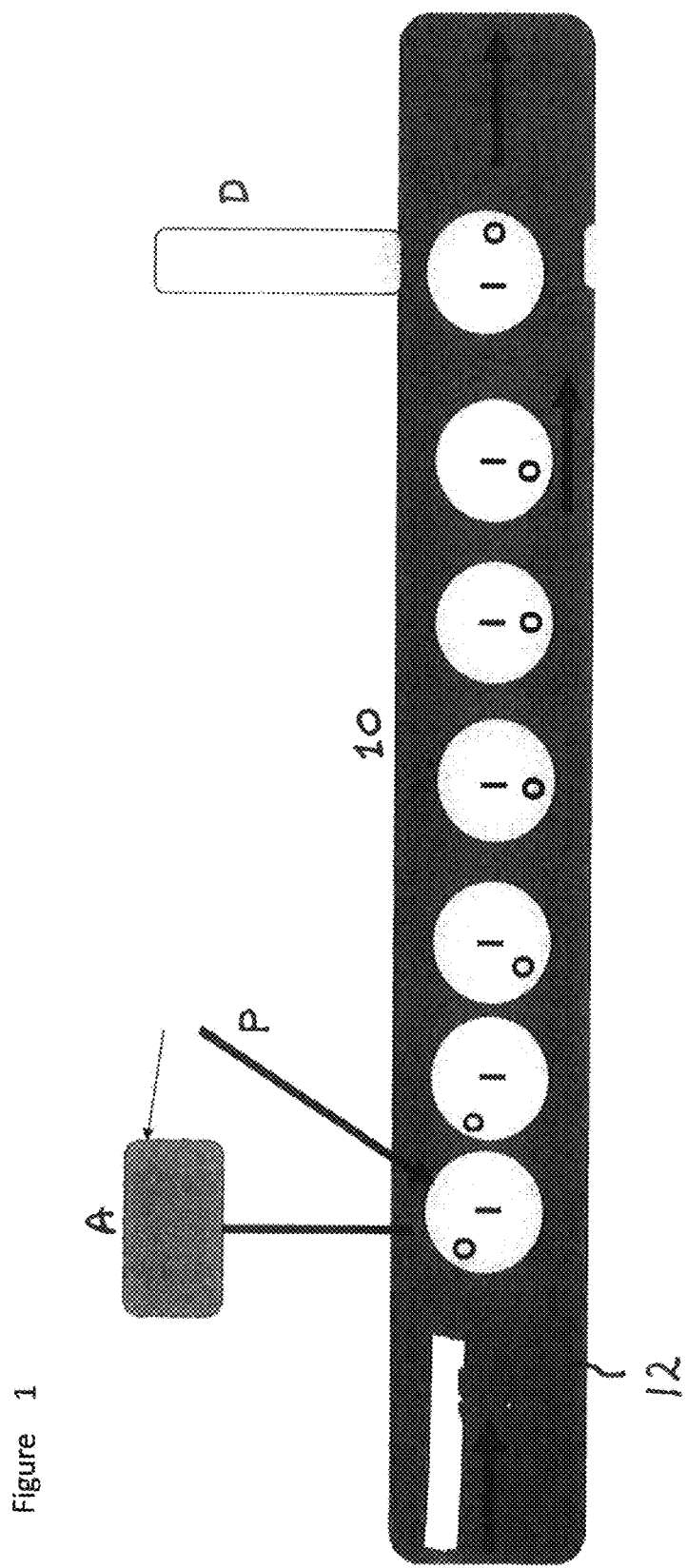
FIG. 1 is a schematic of a pipeline with an internal leak detection mechanism therein.

FIG. 1 is a schematic of a pipeline 10 where crude oil 12 is flowing from left to right as indicated by the arrows. The gas enabled photo sensitive particles are labelled P and are present in the crude oil 12 due to a feeding device A. A UV detector D is present in/on the pipeline 10 in order to receive a signal from the gas enabled photo sensitive particles when they encounter a change state, namely a leak condition in the pipeline 10.

Figure 2:
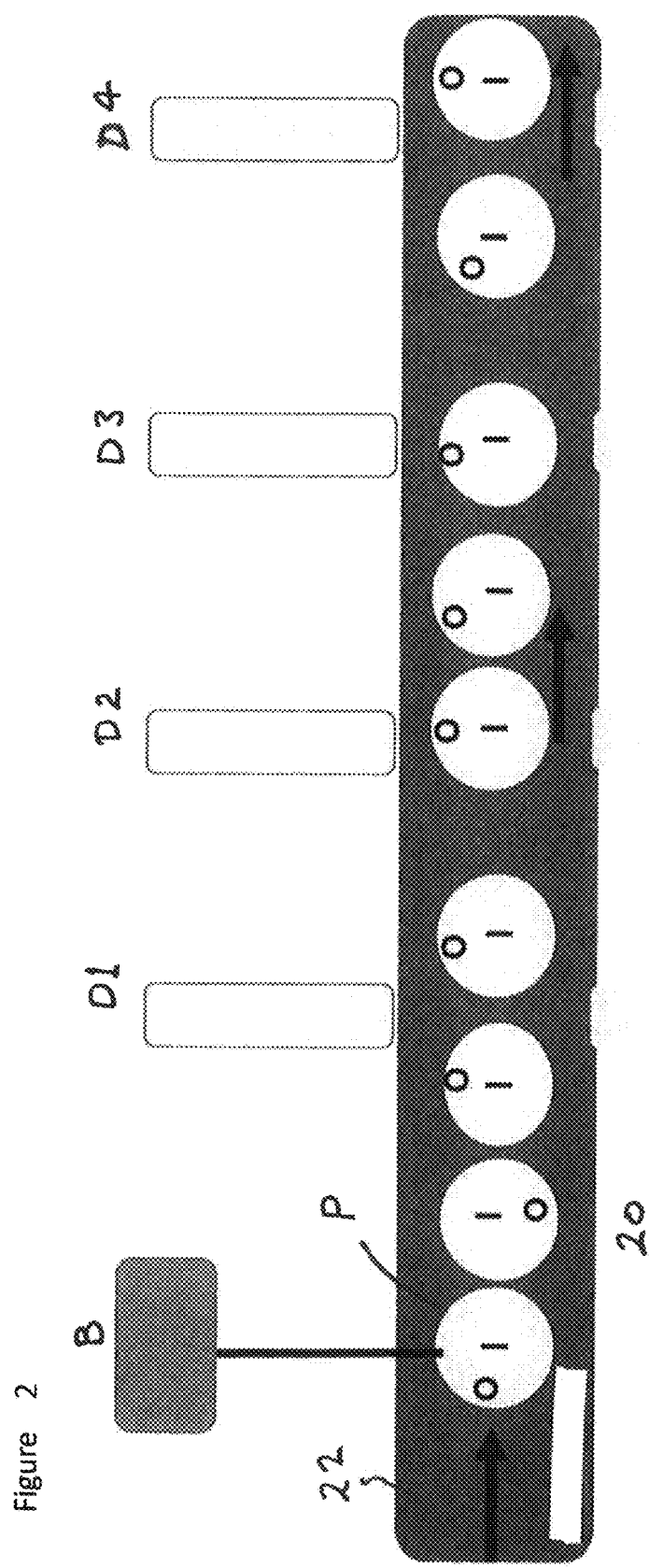
FIG. 2 is a schematic of a pipeline with an array of detectors deployed therein.

FIG. 2 is a schematic of a pipeline 20 whereby crude oil 22 is flowing from left to right as indicated by the arrows. Device B will introduce the gas enabled photo sensitive particles P into the pipeline 20. These particles will flow with the crude oil 22 and pass by the multitude of sensors D1, D2, D3 and D4 which are spaced apart at intervals to allow for detection of leaks along the length of the pipeline 20.

Figure 3:
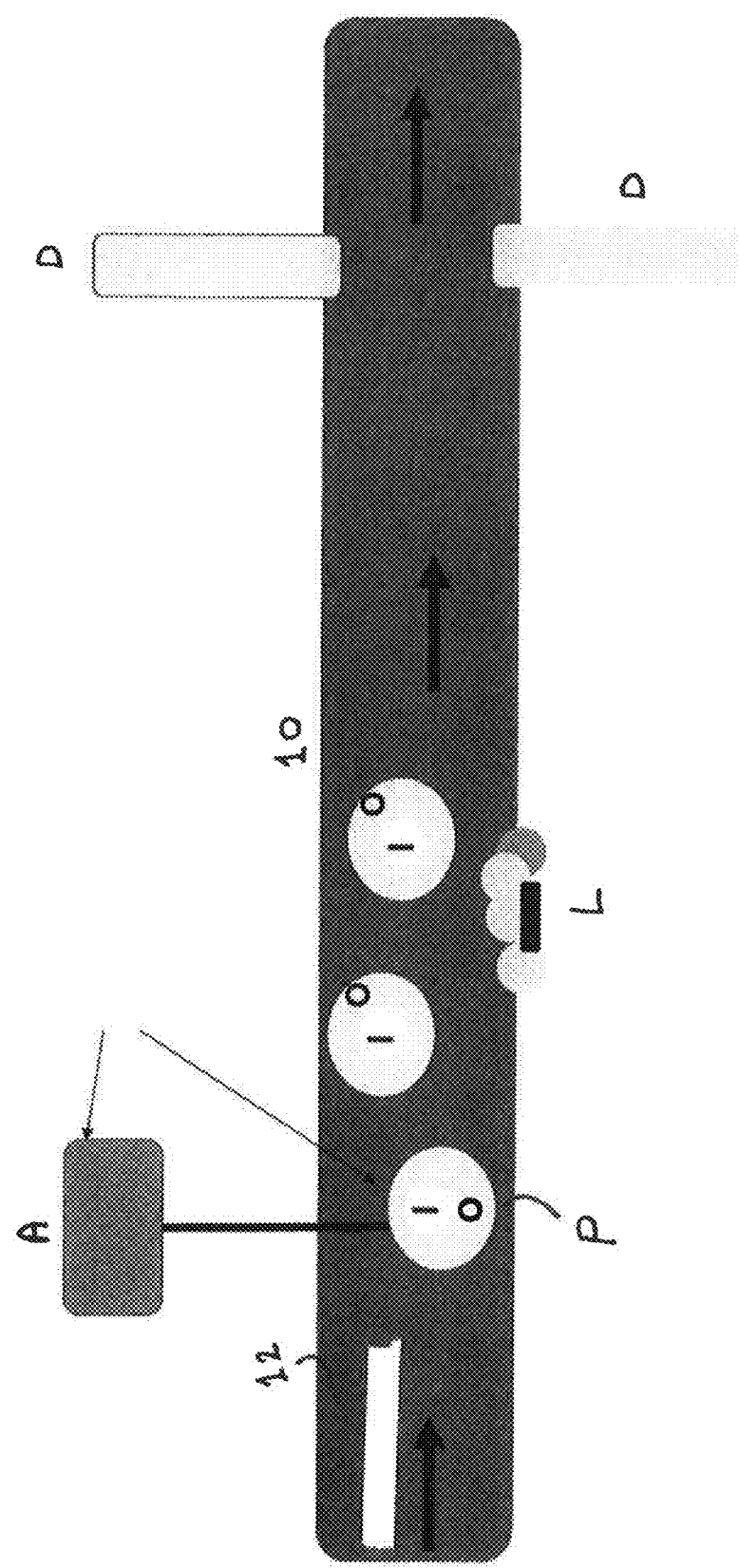
FIG. 3 is a schematic of a pipeline showing the state where particles are quenched and their signal changed.

FIG. 3 Is a schematic of a pipeline according to FIG. 1 wherein crude oil 12 is flowing through a pipeline 10 along the direction of the arrows. A device is present for feeding the gas enabled photo sensitive particles into the crude oil 12. A UV leak detector D is present in/on the pipeline 10 to receive a signal from the gas enabled photo sensitive particles encounter a leak. As seen in FIG. 3, particles denoted as L are present at a leak site within the pipeline 10. The particles will cluster around the leak and since they are encountering a leak condition will change their state and transmit a signal of this changed state to the detector D. The detector will transmit this data to a receiver at a facility overseeing operation of the pipeline and thereby alert an operator that a leak condition is occurring.

This leak detection method is able to accurate alarm when product is released from the pipeline. The particles involved possess a high enough degree of sensitivity to this product release as well as allow for timely detection thereof. Further this method will allow for the operator to identify the leak location and leak rate to prioritize a response.

Figure 4:
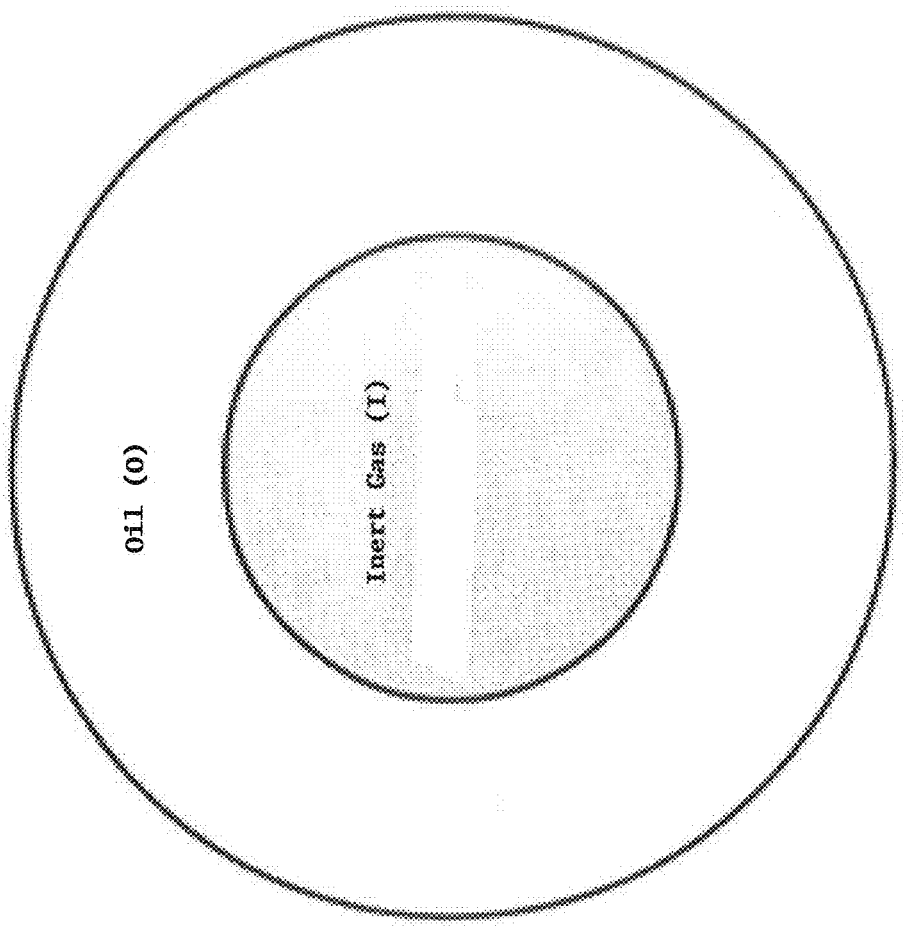
FIG. 4 is a cross sectional view of a gas micro-emulsion particle.

FIG. 4 is a cross sectional representation of one type of gas enabled photo sensitive particle that could be employed in the invention. An inert gas I is surrounded by a hydrocarbon O which when fed to a hydrocarbon system in a pipeline forms an emulsion. This emulsion will allow for the ready delivery of a gas enabled photo sensitive particle to the hydrocarbon in the pipeline as the hydrocarbon O dissolves within the hydrocarbon system in the pipeline.

Figure 5:
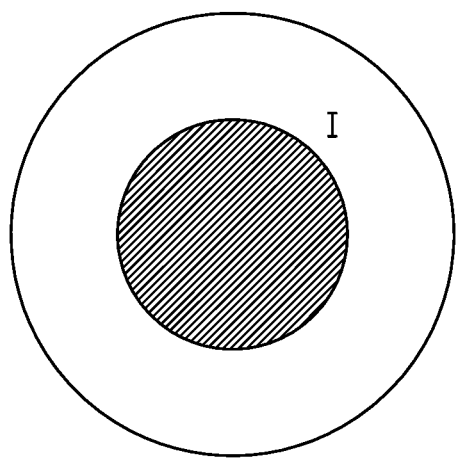
FIG. 5 is a cross sectional view of an inert gas stabilized on micro solid particle.

FIG. 5 is a cross sectional representation of another type of gas enabled photo sensitive particle that could be employed in the invention. The inert gas I surrounds the particle identified by the dark filled in circle which will be released as gas enabled photo sensitive particle when this system is introduced into the hydrocarbon system in a pipeline.

Figure 6:
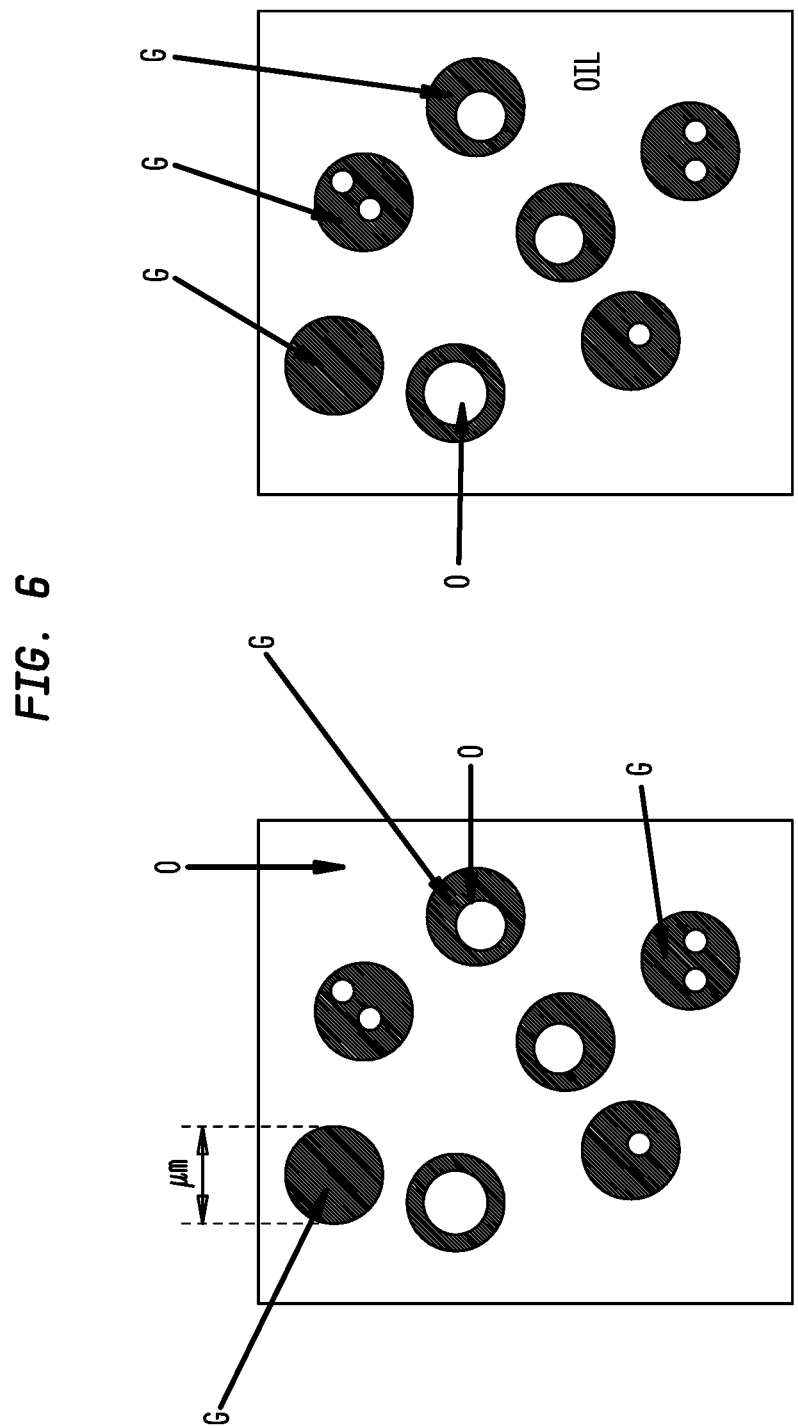
FIG. 6 is a schematic representation of the particles in the oil-gas-oil emulsion.

FIG. 6 is a cross sectional representation of the oil-gas-oil emulsion as employed in the invention. As indicated the size of the emulsion particle is about 1 micron in diameter. The oil O that is present in the pipeline that is being transported is the primary phase. The gas G is represented by the circles present in the oil O phase. Typically, this is an inert gas such as nitrogen and argon, and this inert gas will be surrounded by the gas enabled photo sensitive particles. The circle(s) within the circles represented by O as well are more of the oil, thereby comprising the oil-gas-oil emulsion which can be used to deliver the gas enabled photo sensitive particles to the pipeline containing the oil.

Thus, the oil-gas-oil emulsion is for example, a solid nano or micro silica or zinc oxide core particle (the gas enabled photo sensitive particle) that surrounds an inert gas core such as nitrogen or argon gas. The inert gas would contain the oil and the emulsion is completed by the primary phase oil present in the pipeline. The resulting oil-gas-oil emulsion would be aided by surfactants such as non-ionic surfactants When this oil-gas-oil emulsion emulsifies, the gas enabled photo sensitive particles will enter the oil phase within the pipeline and will operate to provide information about leaks to the operator of the pipeline.

While this invention has been described with respect to particular embodiments thereof, it is apparent that numerous other forms and modifications of the invention will be obvious to those skilled in the art. The appended claims in this invention generally should be construed to cover all such obvious forms and modifications which are within the true spirit and scope of the invention.

Having thus described the invention, what I claim is:

1. A method for detecting a leak in a liquid pipeline comprising feeding gas enabled photo sensitive particles into the liquid pipeline wherein the gas enabled photo sensitive particles are particles that surround an inert gas and the particles in turn are surrounded by a surfactant or liquid active system.

2. The method as claimed in claim 1 wherein a liquid flowing in the liquid pipeline is selected from a group consisting of crude oils, petrochemical products, natural gas liquids, monomers, ethylene, diesel, gasoline and jet fuel.

3. The method as claimed in claim 1 wherein each of the particles is a nano-particle or micro-particle.

4. The method as claimed in claim 3 wherein the nano-particle or micro-particle is selected from the group consisting of a silica particle and a zinc oxide particle.

5. The method as claimed in claim 1 wherein the inert gas is selected from the group consisting of nitrogen and argon.

6. The method as claimed in claim 1 wherein the surfactant is selected from the group consisting of sodium dodecyl sulfates, triblock copolymers PEO-PPO-PEO (poly(ethylene oxide)-poly(propylene oxide)-poly(ethylene oxide)), polyoxyethylene, alkylphenate, polytetrafluoroethylene (PTFE) and OTFE, ethoxylated alcohol, and polyethylene (PEG) surfactants.

7. The method as claimed in claim 1 further comprising a hydrocarbon layer on the surfactant or liquid active system.

8. The method as claimed in claim 1 wherein the gas enabled photo sensitive particles are an oil-gas-oil emulsion.

9. The method as claimed in claim 1 wherein the gas enabled photo sensitive particles change their luminescent state when a leak condition is encountered.

10. The method as claimed in claim 9 wherein a detector detects the change in luminescent state.

11. The method as claimed in claim 10 wherein the detector detects the photo sensitive particles in the liquid thereby establishing a steady state reading.

12. The method as claimed in claim 10 wherein the detector sends the steady state reading and change in the luminescent state reading to a supervisory control and data acquisition system.

13. The method as claimed in claim 12 wherein the supervisory control and data acquisition system compares the steady state reading and the change in the luminescent state reading to calculate if a leak condition is present.

14. The method as claimed in claim 10 wherein the detector is a plurality of detectors mounted periodically along a length of the pipeline.

15. A method for monitoring a liquid pipeline comprising feeding gas enabled photo sensitive particles into the liquid pipeline wherein the gas enabled photo sensitive particles are particles that surround an inert gas and the particles in turn are surrounded by a surfactant or liquid active system.

16. The method as claimed in claim 15 wherein a liquid flowing in the liquid pipeline is selected from a group consisting of crude oils, petrochemical products, natural gas liquids, monomers, ethylene, diesel, gasoline and jet fuel.

17. The method as claimed in claim 15 wherein each of the particles is a nano-particle or micro-particle.

18. The method as claimed in claim 17 wherein the nano-particle or micro-particle is selected from the group consisting of a silica particle and a zinc oxide particle.

19. The method as claimed in claim 15 wherein the inert gas is selected from the group consisting of nitrogen and argon.

20. The method as claimed in claim 15 wherein the surfactant is selected from the group consisting of sodium dodecyl sulfates, triblock copolymers PEO-PPO-PEO (poly(ethylene oxide)-poly(propylene oxide)-poly(ethylene oxide)), polyoxyethlene, alkylphenate, polytetrafluoroethylene (PTFE) and OTFE, ethoxylated alcohol, and polyethylene (PEG) surfactants.

21. The method as claimed in claim 15 further comprising a hydrocarbon layer on the surfactant or liquid active system.

22. The method as claimed in claim 15 wherein the gas enabled photo sensitive particles are an oil-gas-oil emulsion.

23. The method as claimed in claim 15 wherein the gas enabled photo sensitive particles change their luminescent state when a leak condition is encountered.

24. The method as claimed in claim 15 wherein a detector detects the change in the luminescent state.

25. The method as claimed in claim 24 wherein the detector detects the photo sensitive particles in the liquid thereby establishing a steady state reading.

26. The method as claimed in claim 25 wherein the detector sends the steady state reading and change in the luminescent state reading to a supervisory control and data acquisition system.

27. The method as claimed in claim 26 wherein the supervisory control and data acquisition system compares the steady state reading and the change in the luminescent state reading to calculate if a leak condition is present.

28. The method as claimed in claim 24 wherein the detector is a plurality of detectors mounted periodically along a length of the pipeline.

\* \* \* \* \*